United States Patent
Barak

(10) Patent No.: US 6,478,757 B1
(45) Date of Patent: *Nov. 12, 2002

(54) DEVICE FOR PRESSURIZING LIMBS

(75) Inventor: Jakob Barak, Oranit (IL)

(73) Assignee: Medical Compression Systems (D. B. N.), Caesarea (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/038,157

(22) Filed: Mar. 11, 1998

(30) Foreign Application Priority Data

Aug. 31, 1997 (IL) .................................................. 121661

(51) Int. Cl.⁷ ............................................... A61H 19/00
(52) U.S. Cl. ...................... 601/151; 601/148; 606/201; 128/DIG. 20
(58) Field of Search ............................... 601/148–152; 128/DIG. 20; 602/13; 606/201, 202

(56) References Cited

U.S. PATENT DOCUMENTS

| | | | | |
|---|---|---|---|---|
| 2,823,668 A | * | 2/1958 | Court et al. .................. 602/13 |
| 2,880,721 A | | 4/1959 | Corcoran | |
| 2,896,612 A | * | 7/1959 | Bates et al. ................. 601/149 |
| 2,943,859 A | * | 7/1960 | Koski et al. ................. 602/13 |
| 3,454,010 A | * | 7/1969 | Lilligren et al. ............ 601/149 |
| 3,548,809 A | | 12/1970 | Conti | |
| 4,157,713 A | * | 6/1979 | Clarey ......................... 602/13 |
| 4,402,312 A | * | 9/1983 | Villari et al. ................ 601/152 |
| 4,418,690 A | | 12/1983 | Mummert | |
| 4,573,453 A | | 3/1986 | Tissot et al. | |
| 4,597,384 A | * | 7/1986 | Whitney ...................... 601/152 |
| 4,682,588 A | * | 7/1987 | Curlee .......................... 602/13 |
| 4,858,596 A | | 8/1989 | Kolstedt et al. | |
| 5,007,411 A | | 4/1991 | Dye | |
| 5,014,681 A | * | 5/1991 | Neeman et al. ............. 601/152 |
| 5,025,781 A | | 6/1991 | Ferrari | |
| 5,109,832 A | * | 5/1992 | Proctor ........................ 601/149 |
| 5,117,812 A | | 6/1992 | McWhorter | |
| 5,179,941 A | * | 1/1993 | Siemssen et al. ........... 601/152 |
| 5,211,162 A | * | 5/1993 | Gillen, Jr. et al. .......... 601/151 |
| 5,218,954 A | * | 6/1993 | Van Bemmelen ........... 601/151 |
| 5,288,286 A | * | 2/1994 | Davis et al. .................. 602/13 |
| 5,368,547 A | * | 11/1994 | Polando ....................... 601/151 |
| 5,575,762 A | * | 11/1996 | Peeler et al. ................. 601/152 |
| 5,588,955 A | | 12/1996 | Johnson, Jr. et al. | |

(List continued on next page.)

FOREIGN PATENT DOCUMENTS

| | | | | |
|---|---|---|---|---|
| DE | 19 03 217 | | 4/1970 | |
| DE | 27 10 677 | | 9/1978 | |
| DE | 3633937 | * | 5/1987 | .................. 601/152 |
| EP | 388 200 | | 9/1990 | |
| FR | 2 122 734 | | 9/1972 | |
| FR | 2583978 | * | 1/1987 | .................. 601/152 |
| GB | 2 017 508 | | 10/1979 | |
| JP | 38562 | * | 2/1996 | |
| JP | 182771 | * | 7/1997 | |
| SU | 1452523 | * | 1/1989 | .................. 601/152 |

*Primary Examiner*—Justine R. Yu
(74) *Attorney, Agent, or Firm*—Samuels, Gauthier & Stevens, LLP

(57) ABSTRACT

A device for applying pressure to a body limb comprises a sleeve containing individually inflatable cells, each cell being subdivided into longitudinally extending confluent compartments that are inflated and deflated essentially simultaneously. A messaging sleeve, an inflation unit for intermittent inflation of selected cells of the sleeve, and a detecting unit for detecting a temporo-spatial regime of cell inflation are provided. Applications include immobilization of fractured bones, and messaging of limbs to promote blood flow.

7 Claims, 4 Drawing Sheets

U.S. PATENT DOCUMENTS

| | | |
|---|---|---|
| 5,591,200 A | 1/1997 | Cone et al. |
| 5,634,889 A * | 6/1997 | Gardner et al. ............. 601/151 |
| 5,713,954 A | 2/1998 | Rosenberg et al. |
| 5,800,528 A | 9/1998 | Lederman et al. |
| 5,810,750 A * | 9/1998 | Buser ............................ 62/13 |
| 5,843,007 A * | 12/1998 | McEwen et al. ............ 601/152 |
| 5,931,797 A * | 8/1999 | Tumey et al. ............... 601/152 |

* cited by examiner

DEVICE FOR PRESSURIZING LIMBS

FIELD OF THE INVENTION

The present invention relates to medical devices and more specifically to devices for immobilizing or massaging body limbs, for example, in cases of edema, vein disorders such as chronic venous insufficiency (c.v.i.), varicose veins (v.v), varicose ulcers (v.u.) and others; prevention of deep vein thrombosis; and bone fractures.

GLOSSARY

In the following description and claims the terms "sleeve" and "cell" mean:

Sleeve—a hollow cylinder formed of a flexible material into the lumen of which a body limb, e.g. an arm, leg or foot, may be inserted.

Cell—A section of a massaging sleeve which may be inflated or deflated independently of the remainder of the sleeve.

BACKGROUND OF THE INVENTION

In the condition known as edema, interstitial fluid is inadequately drained by the lymphatics. This causes an accumulation of fluid in the affected tissues leading to painful swelling. When this occurs in a body limb, beneficial results are obtained by massaging the limb in such a way as to force the fluid towards the proximal end of the limb and into the trunk of the body. A number of apparatuses have been devised for this purpose, for example, as disclosed in U.S. Pat. Nos. 5,117,812, 5,007,411, 5,025,781 and 5,591,200. In these apparatuses the limb to be treated is inserted into a massaging sleeve having a plurality of essentially circumferential cells along its length. Each cell is capable of being individually inflated by forcing a fluid into the interior of the cell in order to apply pressure to the limb segment contained within the cell. Each cell is made to undergo cycles of inflation and deflation in order to apply intermittent pressure on the limb segment which it encloses thus achieving a massaging effect on the limb. The inflation-deflation cycles of the different cells in the sleeve are typically staggered so as to generate peristaltic contractions of the sleeve, thus moving fluids inside the limb towards the trunk. In addition to being of benefit in cases of edema, these devices are also useful in the treatment of c.v.i., v.v., v.u. and the prevention of deep vein thrombosis.

In prior art devices, each cell in the sleeve, when deflated, forms essentially a circumferential band around the limb, the circumference of which is selected to correspond to the circumference of the limb segment contained within the cell. Upon inflation, the cell assumes essentially a toroidal shape. In this case, a decrease in the inner circumference of a cell upon inflation is accompanied by an essentially identical increase in the outer circumference of the cell. For example, in order to obtain a 36% decrease in the inner circumference of a cell upon inflation, the outer circumference of the inflated cell must be 36% larger than the original circumference of the limb segment contained therein. The fractional decrease in the inner circumference of the cell corresponds to the amount of pressure applied by the inflated cell to the limb segment contained therein. Thus, in order to obtain useful levels of pressure using prior art devices, the sleeve is of necessity very bulky, stiff and uncomfortable in use and relatively large and powerful compression pumps are required. Prior art devices therefore require the individual to be immobilized during treatment for prolonged periods of time.

It is therefore the object of the present invention to provide a limb massaging device in which the aforementioned disadvantages of the prior art devices are substantially reduced or eliminated.

SUMMARY OF THE INVENTION

In accordance with a first aspect of the present invention there is provided a device for applying pressure to a body limb, comprising a sleeve containing a plurality of individually inflatable cells, each cell being subdivided into two or more longitudinally extending confluent compartments which are inflated and deflated essentially simultaneously.

The device according to the invention may, for example, be used to immobilize a fractured bone in a limb by inserting the limb into the sleeve and inflating all the cells thereof so as to render the sleeve rigid and inflexible for the duration of the treatment.

By one mode the invention provides a device for applying pressure to one or more limbs of the body comprising:

(a) a massaging sleeve containing a plurality of individually inflatable cells, each cell being subdivided into two or more longitudinally extending confluent compartments which are inflated and deflated essentially simultaneously;

(b) means for the separate and intermittent inflation of any one of said plurality of inflatable cells; and (c) control means for determining the temporo-spatial regime of cell inflation.

Typically, and by way of a non-limiting example, a temporo-spatial regime of cell inflation is selected which generates peristaltic contractions of the sleeve. For example, with a sleeve containing 5 cells numbered consecutively from the distal to the proximal end of the limb, cell 1 would first be inflated, followed by cell 2. Cell 1 would then be deflated and cell 3 inflated. Next, cell 2 is deflated as cell 4 is inflated, and then cell 3 is deflated and cell 5 inflated. Finally, cell 4 and then cell 5 are deflated and the cycle begins again. Other temporo-spatial regimes of cell inflation are also contemplated within the scope of the invention.

In accordance with a third aspect of the present invention there is provided a method of massaging a limb of the body of an individual comprising: inserting the limb to be treated into a massaging sleeve of the kind specified and inflating the cells of the sleeve according to a predetermined temporo-spatial regime.

The device according to the invention is applied for example, in cases of edema, c.v.i., v.v., v.u. or preventing deep vein thrombosis.

As will become evident through the description below, subdividing the cells of the sleeve into compartments according to the present invention yields several advantages over prior art devices. Since the diameter of the inflated sleeve is not substantially larger than the diameter of the treated limb, the sleeve may be worn under clothing and is thus concealed during use. Moreover, the sleeve remains flexible and comfortable during use so that the individual need not be immobilized during treatment. Furthermore, the volume of the inflated cells in the present invention is substantially less than in prior art devices, so that a much smaller compressor need be used for inflating the cells. This in turn allows the controlling unit to be substantially lighter than is required for prior art devices. These features allow the individual to be completely ambulatory during treatment.

While in the description given below, the cells in the sleeve are aligned to form an elastic cylinder, the invention is not bound by this constraint and other types of sleeves are contemplated within the scope of the invention. For example, the sleeve may initially be a pad which is wrapped around the limb into an essentially cylindrical shape and then fastened in this configuration by various means.

In operation, a cell is inflated by forcing a fluid into the interior of the cell between the inner and outer shells. While in the description given below a deflated cell forms an essentially circumferential band around the limb, and the fluid used to inflate the cell is air, the invention is not bound by these constraints, and other cell shapes and fluids are contemplated within the scope of the invention.

BRIEF DESCRIPTION OF THE DRAWINGS

The invention will now be demonstrated by way of a non-limiting example, with reference to the accompanying drawings in which.

DESCRIPTION OF A SPECIFIC EMBODIMENT

In the following, an embodiment of the invention will be described for use on the leg of an individual. However, it is to be understood that the invention is also intended for use on any body limb such as an arm, a foot, a part of a leg, arm or foot, and may be used on two or more limbs simultaneously.

Figure 1:
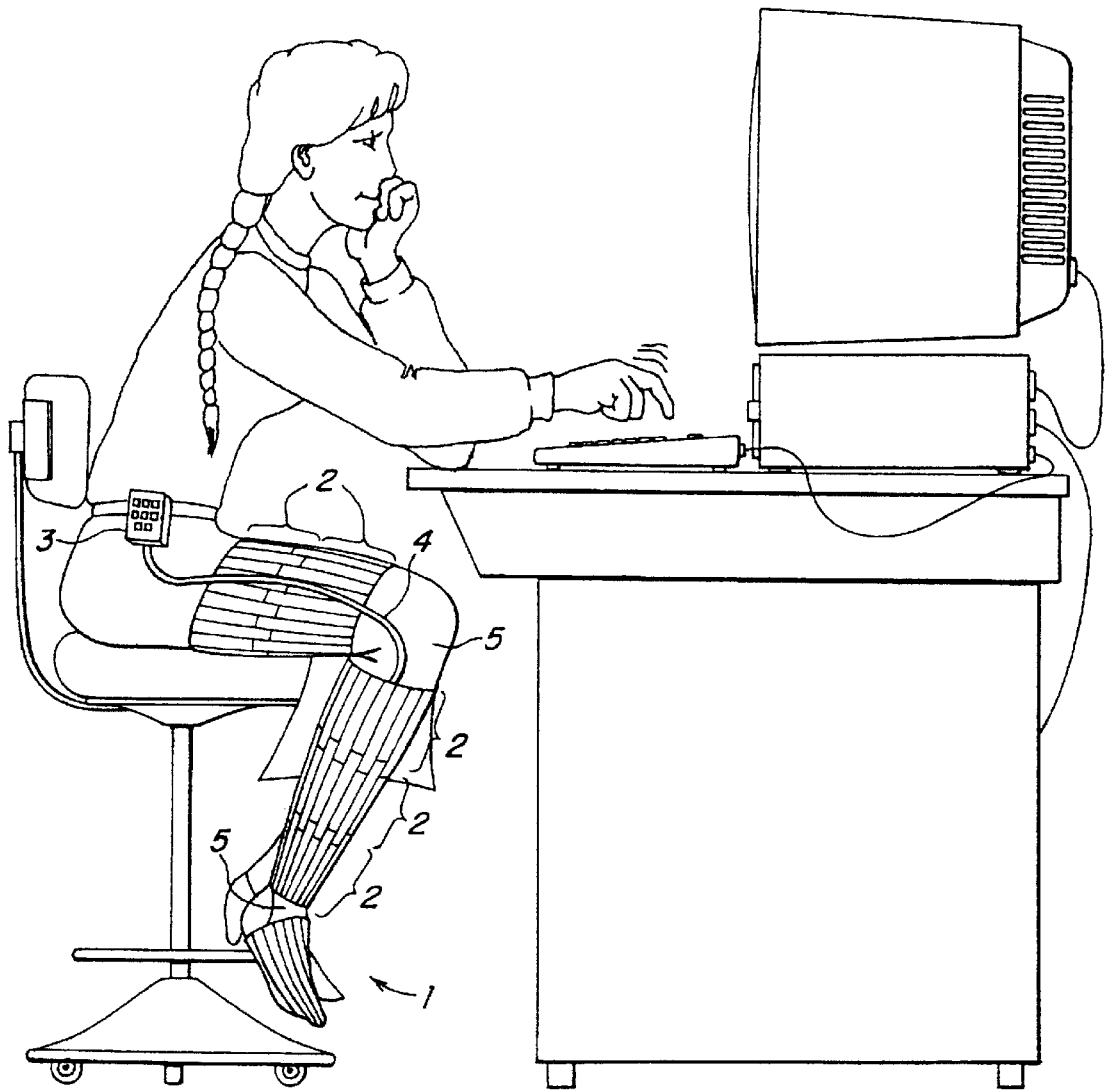
FIG. 1 shows a massage sleeve according to the invention in use on the leg of an individual.

In FIG. 1, a patient is depicted wearing a massaging sleeve 1 of the invention on her leg while carrying out her routine duties. In FIG. 1, the trouser leg of the patient is cut away to reveal the sleeve. In practice, however, the sleeve remains concealed from view, and due to the facets of the present invention remains unnoticed even during operation when the cells are intermittently inflated. The sleeve 1 has an inner and outer surface composed of a durable flexible material and is divided into a plurality of cells 2 along its length and each cell is connected to the control unit 3 by a separate tube collectively labeled 4 in FIG. 1. Sections of the sleeve may be of non-inflatable elastic materials 5, for example around the knee and ankle 5.

Figure 2:
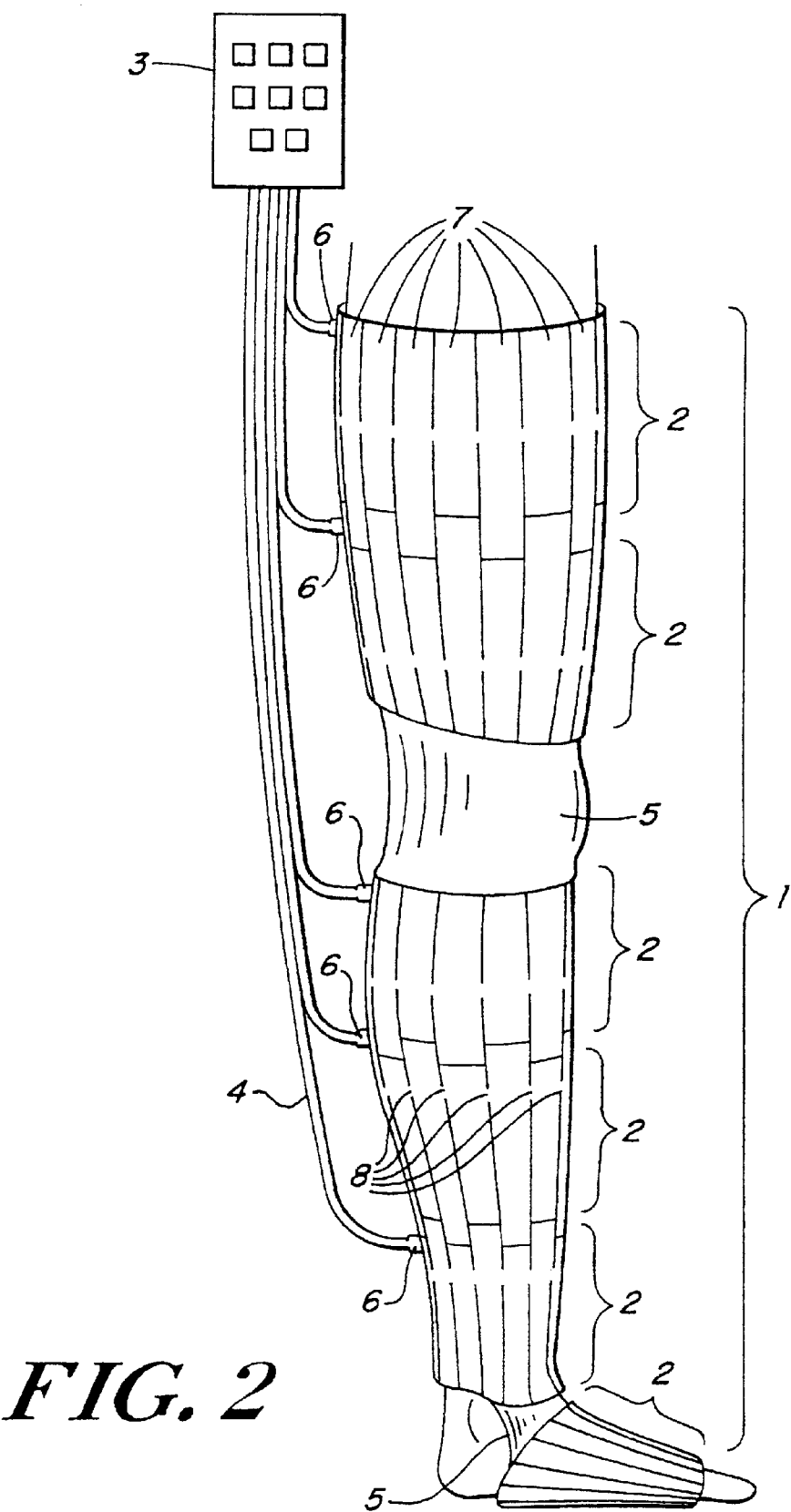
FIG. 2 shows a massage sleeve according to the invention mounted on the leg of an individual drawn to a larger scale.
Figure 3:
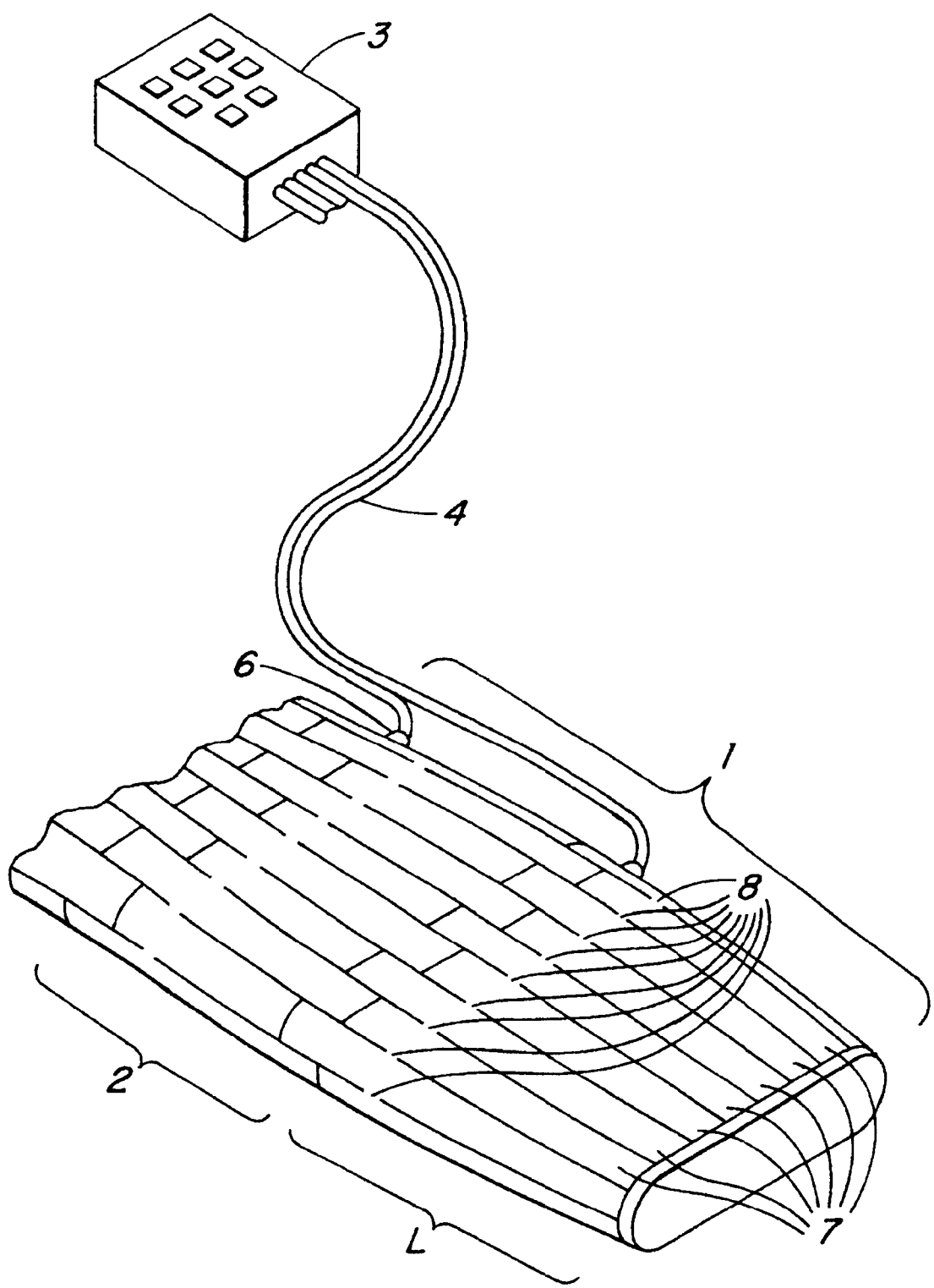
FIG. 3 shows a fractional perspective view of a massage sleeve according to the invention fitted with a control unit.

As can be seen in FIGS. 2 and 3, each cell has a fluid inlet opening 6 to which a hose 4 from the control unit 3 is attached. The control unit 3 contains a compressor capable of compressing and pumping ambient air into one or more selected cells in the sleeve via the hoses 4. The control unit 3 allows a temporo-spatial regime of inflation and deflation of the cells to be selected, e.g. a regime which generates peristaltic contractions of the sleeve so as to force fluids inside the limb towards the proximal end of the limb, or a regime which enhances the flow of the venous blood in the limb. The continuity of the peristalsis is enhanced by inter-digitating the compartments of adjacent cells in the massaging sleeve as shown in FIGS. 2 and 3.

In accordance with the present invention, the cells are subdivided into a plurality of longitudinally extending compartments 7. The compartments are formed, for example, by welding the inner and outer shells of the massaging sleeve along the boundaries of the compartments. The compartments in a given cell are confluent due to perforations 8 in the seams between adjacent compartments so that all the compartments in the cell are inflated or deflated essentially simultaneously. Each compartment, when inflated, assumes essentially the shape of a cylinder having its axis parallel to that of the limb.

Figure 4A:
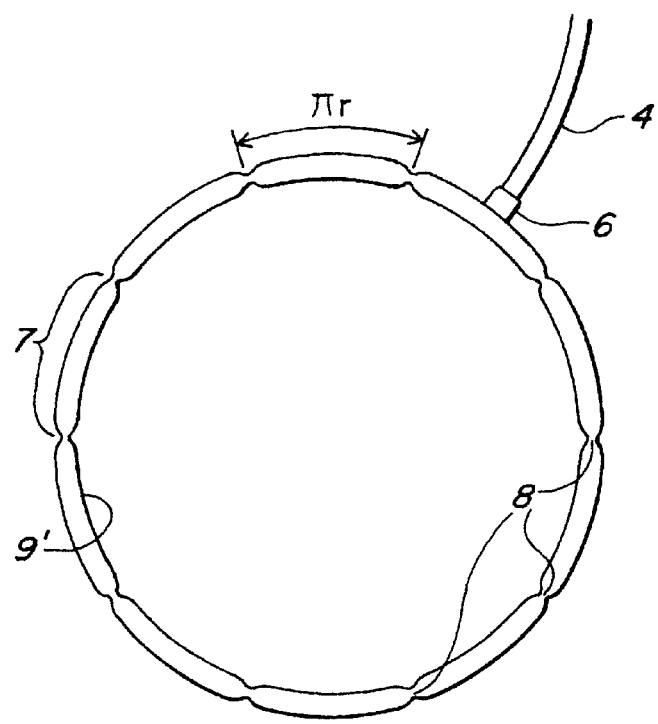
FIGS. 4a and 4b show a cross-section of a cell in the deflated and inflated states, respectively.
Figure 4B:
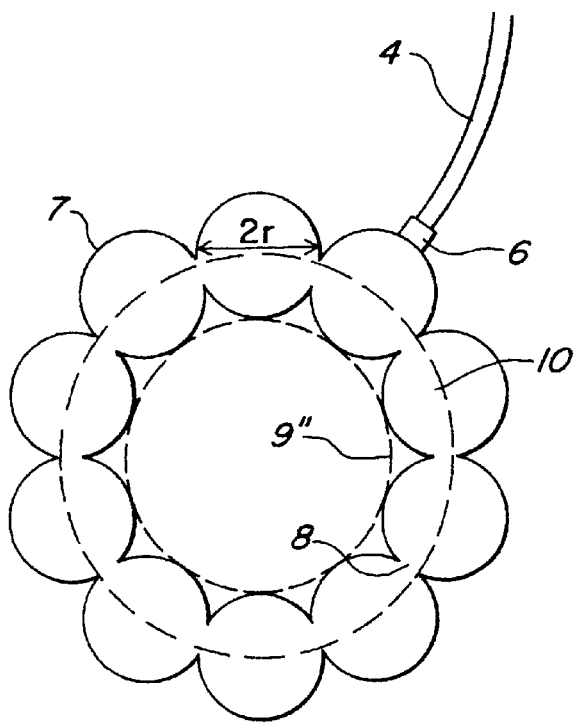

A cross-section of a deflated cell is shown in FIG. 4a, and FIG. 4b shows the same cross-section after inflation. The cell has been divided, by way of example, into ten identical compartments, it being self-evident that any other number of compartments may be used. If N is the number of compartments in a given cell, and r is the radius of an inflated compartment, then as can be seen in FIG. 4b the length of the circumference 10 that passes through the centers of the inflated compartments will be 2Nr, whereas the circumference 9' of the deflated cell is Nπr. The fractional decrease in the circumference upon inflation is thus $$\frac{N\pi r - 2Nr}{\pi N r} = 1 - \frac{2}{\pi} = 0.36 \tag{1}$$

The length of the inner circumference 9'' of the inflated cell will be less than 2Nr so that the fractional decrease in the inner circumference upon inflation is thus greater than 0.36.

N and r are chosen so that πNr (the circumference of the deflated cell) corresponds to the original circumference of the limb segment contained within the lumen of the cell. The fractional decrease in the circumference of the cell upon inflation (0.36) causes a contraction of the cell whereby pressure is applied to the limb which, as follows from equation (1) above, is independent of N and r. Thus, by choosing N sufficiently large, and r correspondingly small, a sleeve is obtained having an inflated outer circumference not substantially larger than the original circumference of the limb. This is in contrast to prior art devices which, as shown above, must have a circumference 36% greater than the initial circumference of the limb in order to achieve the same applied pressure as that produced by the present invention.

Letting now L be the length of a cell and C=Nπr, the initial circumference of the limb contained within the cell, it is readily appreciated from FIG. 4 that the initial volume of the limb contained within the deflated cell is $$V_D = \pi \left(\frac{C}{2\pi}\right)^2 L.$$

The final volume of the limb contained within the inflated cell is less than $$V_I = \pi \left(\frac{0.64C}{2\pi}\right)^2 L = 0.41 V_D.$$

Inflating the cell thus leads to a decrease in the volume of the limb contained within the cell of about 59%. This represents the volume of fluid squeezed out of the limb, or the work performed by the sleeve. This is accomplished by inflating the compartments of the cell to a total volume of $V_T = N\pi r^2 L =$ $$N\pi \left(\frac{C}{N\pi}\right)^2 L = \frac{C^2 L}{N\pi}.$$

In contrast to this, obtaining the same decrease in the volume of the limb by prior art methods requires inflating a cell to a final volume of $$V_F = \pi\left\{\left(\frac{1.36C}{2\pi}\right)^2 - \left(\frac{0.64C}{2\pi}\right)^2\right\}L = \frac{C^2 L}{2.8\pi}. \qquad 5$$

Thus, when the number of compartments in the cell of the present invention is at least 3, the volume to which the cell must be inflated is less than that of prior art devices. Moreover, by choosing N sufficiently large, a decrease of 59% in the volume of the limb can be obtained by inflating the cell to an arbitarily small total volume. For example, when N=30, the total volume of the inflated cell is less than one-tenth of the volume of the inflated cell of the prior art devices. This allows a much smaller compressor to be used than is possible with prior art sleeves, thus permitting the patient to be ambulatory while being treated by the invention.

It is noted that a sleeve according to the invention, e.g. such as sleeve 1 in FIGS. 1 and 2 or a smaller sleeve covering only a portion of a limb, may be used for immobilization of a fractured bone in a limb.

What is claimed is:

1. A device for applying pressure to a body limb having a primary axis comprising:

first and second inflatable cells, each of the first and second cells including at least three intra-cell compartments; said intracell compartments being confluent, each compartment being elongated along a longitudinal axis and being substantially rectangular in shape when deflated and substantially cylindrical in shape when inflated, the longitudinal axes of the compartments substantially aligning with the primary axis of the limb, the first and second cells being longitudinally adjacent each other, and arranged coaxially with respect to the primary axis of the limb, the first and second cells being intermittently inflatable to apply pressure to the limb, wherein the inflatable cells each comprise inner and outer shells of durable flexible material, said inner and outer shells being bonded together about a perimetric cell bond to define the inflatable cell therebetween, said inner and outer shells being further bonded together along compartmental bonds within the perimetric cell bond to define the plurality of intra-cell compartments, wherein the perimetric cell bond includes upper and lower perimetric cell bonds extending substantially in a lateral direction, and left and right perimetric cell bonds extending substantially in the longitudinal direction, and wherein the compartmental bonds partly extend between the upper and lower perimetric cell bonds, wherein the compartmental bonds include perforations to allow for confluent air flow between compartments within a cell, neighboring compartments along a lateral axis sharing a common border and being spatially fixed relative to each other, such that upon inflation of a cell, the cell becomes circumferentially constricted, the first and second cells being non-confluent such that that the first and second cells are separately inflatable, said intra-cell compartments of the first and second cells being interdigitated;

means for laterally coupling outermost compartments so as to form a sleeve, such that the sleeve has a circumference of Nπr when the cell is deflated, and such that the sleeve has a circumference of 2Nr when the cell is inflated, where N is the number of compartments in the cell, and where r is the cross-sectional radius of each compartment when inflated, so as to provide for circumferential constriction;

inflating means for intermittently inflating the first and second cells; and control means for determining the temporo-spatial regime of cell inflation.

2. The device of claim 1 wherein the fractional decrease in the circumference upon inflation is 0.36.

3. The device of claim 1 wherein the bond comprises a weldment.

4. The device of claim 1 wherein adjacent compartments are contiguous.

5. The device of claim 1 wherein the perforations are located adjacent the perimetric cell bond.

6. The device of claim 1 wherein the perforations are located between compartmental bonds extending from the upper and lower perimetric bonds.

7. The device of claim 1 further comprising a fluid inlet to provide for inflation and deflation of the cell.

* * * * *